US00PP07896P

United States Patent [19]

Zaiger et al.

[11] Patent Number: Plant 7,896

[45] Date of Patent: Jun. 30, 1992

[54] PLUM TREE BLACK JACK

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 635,978

[22] Filed: Dec. 31, 1990

[51] Int. Cl.[5] ..... A01H 5/00

[52] U.S. Cl. ..... Plt./38

[58] Field of Search ..... Plt./38

*Primary Examiner*—James R. Feyrer

[57] ABSTRACT

A new and distinct variety of plum tree which has the unique combination of desirable features.

1. Heavy and regular production of fruit.
2. Fruit with large size and attractive dark bluish black skin color.
3. Fruit with good flavor and eating quality.
4. Nearly uniform size of fruit throughout the tree.
5. Vigorous upright growth.
6. Good shipping and storage quality of fruit.

1 Drawing Sheet

ORIGIN OF THE VARIETY

The new and distinct variety of plum tree was originated by us in the experimental orchard located near Modesto, Calif., as an open pollinated seedling of Friar Plum (non-patented). The selection was made from a large group of seedlings growing from seed collected from the self sterile Friar Plum tree which was growing among numerous selections of plum trees in our experimental orchard. One such seedling, which is the present variety, being especially desirable with respect to its fruit was selected for asexual reproduction and commercialization.

ASEXUAL REPRODUCTION OF THE VARIETY

The present new and distinct variety of plum tree was asexually reproduced by budding as performed by us in our experimental orchard located near Modesto, Calif., and shows that all characteristics are established and come true to form through succeeding propagations.

SUMMARY OF THE VARIETY

Our new and distinct variety of plum tree is of large size, vigorous upright growth, and a productive and regular bearer of large, firm, semi-clingstone fruit with good flavor and eating quality. The fruit is further characterized by having an attractive dark bluish-black skin color, good storage and shipping quality and in comparison to Friar Plum (non-patented) is more round in shape and matures approximately 30 days earlier.

DESCRIPTION OF THE PHOTOGRAPHS

The accompanying photographs show reproductions in color of typical specimens of the foliage and fruit of our new plum variety with the upper and lower surface of the leaves being illustrated, an exterior and sectional view of the fruit with a fruit divided in the suture plane to reveal flesh coloration and showing a stone remaining in place. The photographic illustrations were taken shortly after being picked at maturity (firm ripe) and the colors are as nearly true as reasonably possible in a color representation of this type.

DESCRIPTION OF THE VARIETY

The following is a detailed botanical description of the new and distinct variety of plum tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Bearer.*—Regular.

Trunk:
- *Size.*—Medium to large.
- *Surface.*—Shaggy.
- *Color.*—Brown to dull brown (5-E-3) to (6-F-4).

Branches:
- *Angles.*—Moderately narrow.
- *Size.*—Medium.
- *Surface.*—Medium rough.
- *Lenticals.*—Medium number. Small size.
- *Color.*—Grayish brown to dull brown (6-E-3) to (6-F-4).

Leaves:
- *Size.*—Medium to large. Average length — 5". Average width — $1\frac{3}{8}$".
- *Form.*—Oblanceolate.
- *Texture.*—Smooth.
- *Margin.*—Finely serrate.
- *Petiole.*—Size — medium. Medium length. Medium thickness.
- *Glands.*—Globose. Number varies from 0 to 3. Average number 2. Primarily positioned on base of leaf.
- *Color.*—Upper surface — green to dark green (27-F-6) to (27-F-8). Lower surface — grayish green to green (27-D-7) to (27-E-7).

Flower buds:
- *Size.*—Medium.
- *Length.*—Medium.
- *Form.*—Medium to short. Plump.

Flowers:
- *Blooming period.*—First bloom — Feb. 26, 1990. Last bloom — Mar. 7, 1990. Varies slightly due to weather conditions.
- *Pollen.*—Present.
- *Color.*—White.

*Size.*—Medium.

Fruit:

*Maturity when described.*—Firm ripe.

*Date of first picking.*—Jun. 18, 1990.

*Date of last picking.*—Jun. 25, 1990.

*Pollination.*—Viable pollen is produced but the tree is self-sterile.

*Size.*—Large — comparatively uniform. Average diameter axially — 2⅝". Average transversely in suture plane — 2⅝".

*Form.*—Globose.

*Suture.*—Shallow — extends from base to apex.

*Ventral surface.*—Nearly round, very slightly lipped.

*Cavity.*—Rounded to slightly elongated in suture plane. Average depth — ⅜". Average breadth — ½".

*Apex.*—Retuse.

*Base.*—Retuse.

Skin:

*Thickness.*—Medium.

*Texture.*—Medium to tough — tenacious to flesh.

*Tendency to crack.*—Very slight.

*Bloom.*—Moderate.

*Down.*—Wanting.

*Color.*—Varies from dark violet to bluish black (18-F-2) to (19-F-2).

Flesh:

*Texture.*—Firm.

*Juice.*—Moderate.

*Ripens.*—Relatively even, only slightly earlier near apex.

*Flavor.*—Good — mild, good balance between acid and sugar.

*Eating quality.*—Good.

*Fibers.*—Very small — tender.

*Color.*—Pale yellowish white to yellowish white (2-A-2) to (3-A-2). Slight bleeding near apex from skin toward seed of violet brown (11-E-4) to (11-E-5) in some fruit.

Stone:

*Type.*—Semi-clingstone, nearly free.

*Size.*—Medium. Average length — 1⅛". Average width — ¾". Average thickness — ½".

*Form.*—Oval.

*Apex.*—Acuminte.

*Base.*—Straight to rounded.

*Sides.*—Nearly equal — suture side slightly larger.

*Surface.*—Small irregular furrows, heavier to base with slight ridges near ventral surface.

*Tendency to split.*—None.

*Color.*—Light brown to brownish orange (6-B-5) to (6-C-5).

Use:

*Market.*—Local and long distance. Dessert.

Storage quality: Good.

Shipping quality: Good.

The new and distinct variety of plum tree, its flowers and fruit herein described may vary in slight detail due to climatic, soil condition and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous upright growth and being a productive and regular bearer of large, firm, semi-clingstone fruit with good flavor and eating quality; the fruit is further characterized by being nearly globose in shape, with an attractive dark bluish black skin color, having good storage and shipping quality and in comparison to Friar Plum (non-patented) being more round in shape and maturing approximately 30 days earlier.

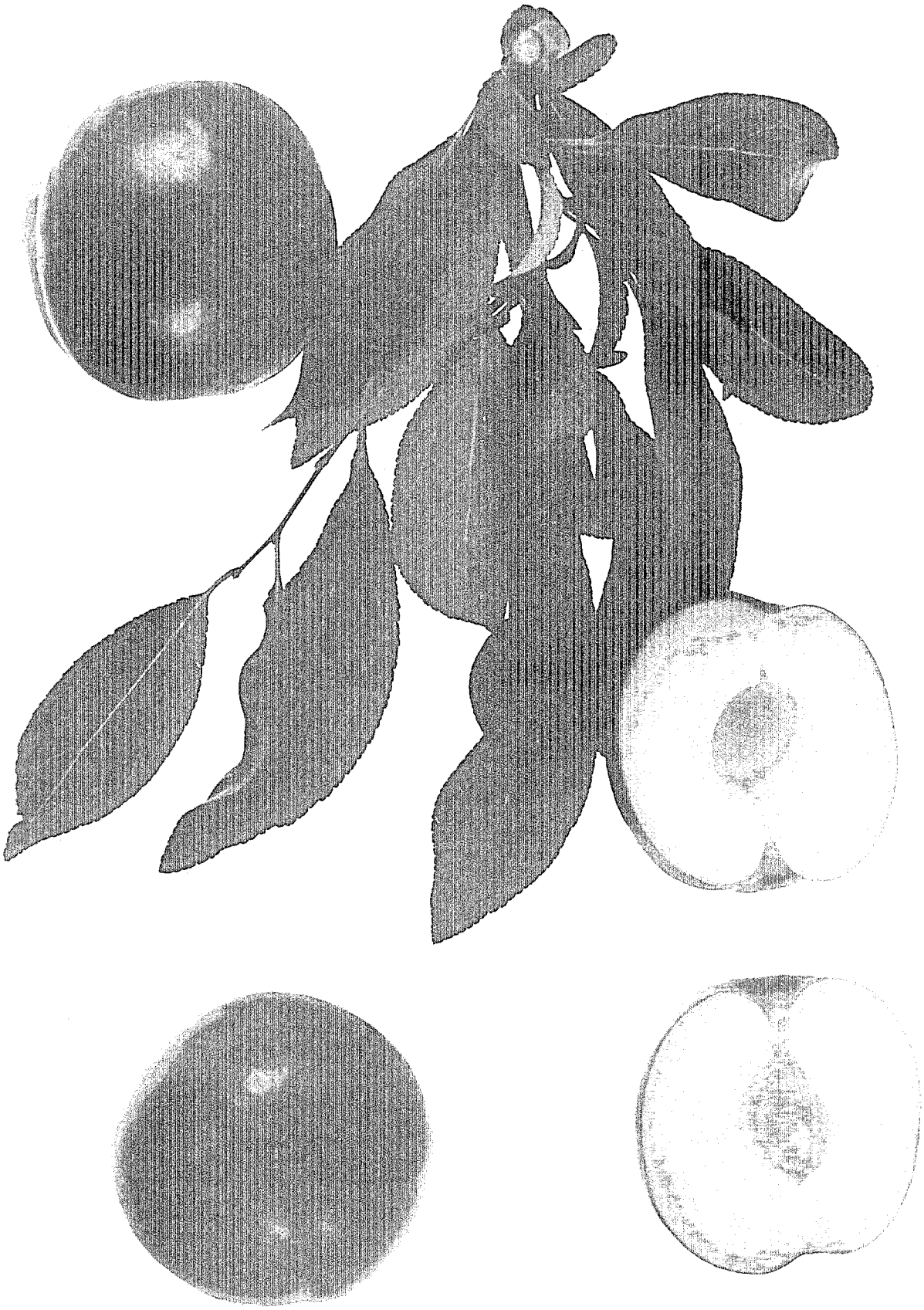

* * * * *